United States Patent [19]

Mesmer

[11] Patent Number: 4,799,779
[45] Date of Patent: Jan. 24, 1989

[54] MICROSCOPE DRAPE

[76] Inventor: Jeffrey C. Mesmer, 4191 Deepwood La., Cincinnati, Ohio 45245

[21] Appl. No.: 171,682

[22] Filed: Mar. 22, 1988

[51] Int. Cl.$^4$ .................. B65D 85/38; B65D 65/02
[52] U.S. Cl. .................................. 350/585; 206/305; 206/316; 150/52 R
[58] Field of Search ............... 350/582, 585; 206/305, 206/316, 634; 150/52 R

[56] References Cited

U.S. PATENT DOCUMENTS

| | | | |
|---|---|---|---|
| 3,528,720 | 9/1970 | Treace | 350/585 |
| 3,698,791 | 10/1972 | Walchle et al. | 350/585 |
| 4,266,663 | 5/1981 | Geraci | 350/585 |
| 4,561,540 | 12/1985 | Hunter et al. | 350/587 |

Primary Examiner—John K. Corbin
Assistant Examiner—Ronald M. Kachmarik
Attorney, Agent, or Firm—Rodman & Rodman

[57] ABSTRACT

The microscope drape includes a one-piece seamless, substantially tubular main body portion. One or more separately formed sleeve-like extensions are joined to the main body portion with a reinforcing member provided at the joint. The reinforcing member is annular and defines a predetermined stress path to permit the drape to withstand a predetermined level of stress at the joint between the main body portion and the sleeve-like extension, and direct stress at the joint along the predetermined stress path. Thus, tension stresses imposed on a drape and the sleeve-like extension are distributed along a uniform stress path defined by the reinforcement member to help ensure against any rips or ruptures in this area when the drape is secured around the microscope.

20 Claims, 6 Drawing Sheets

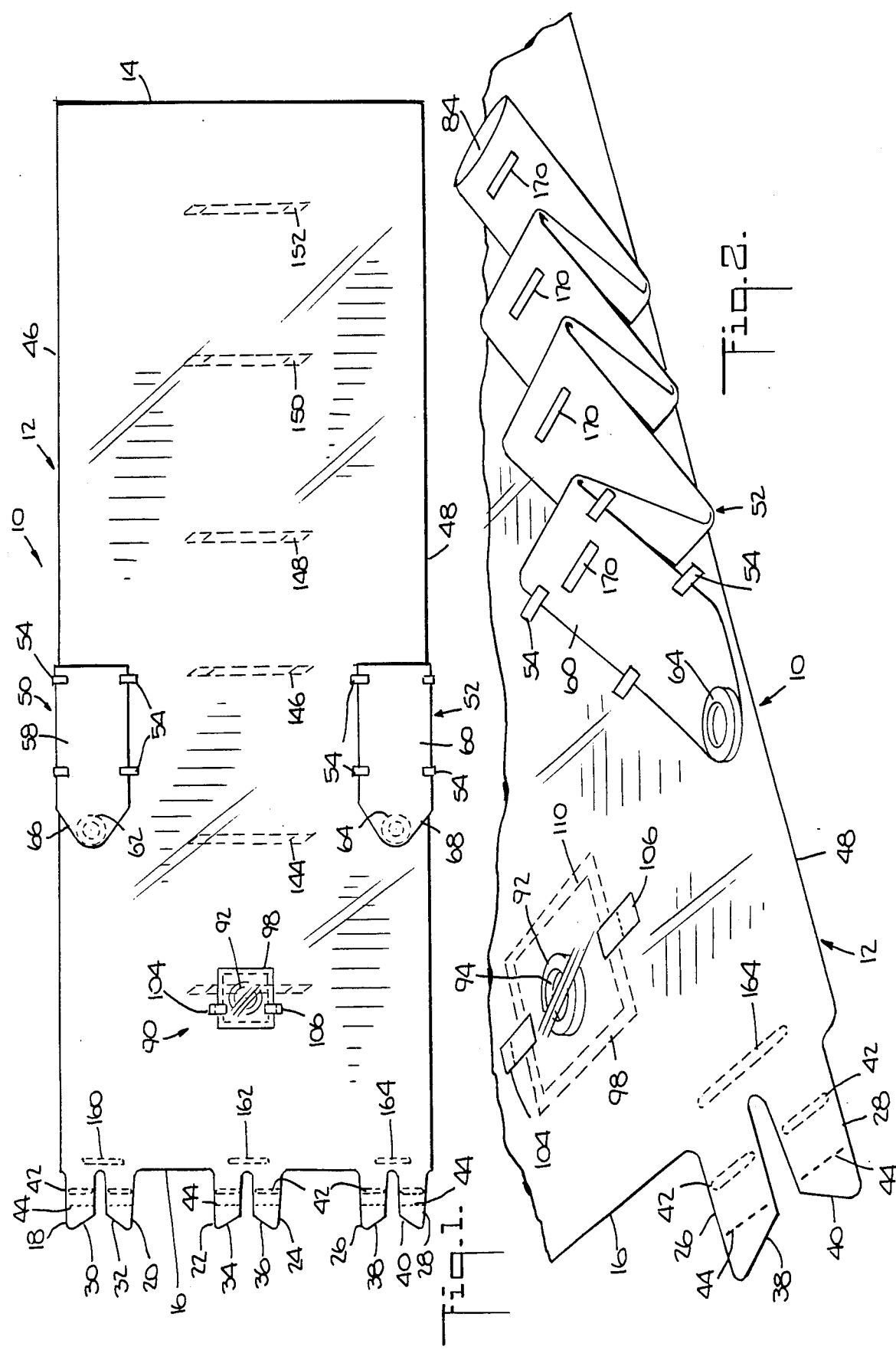

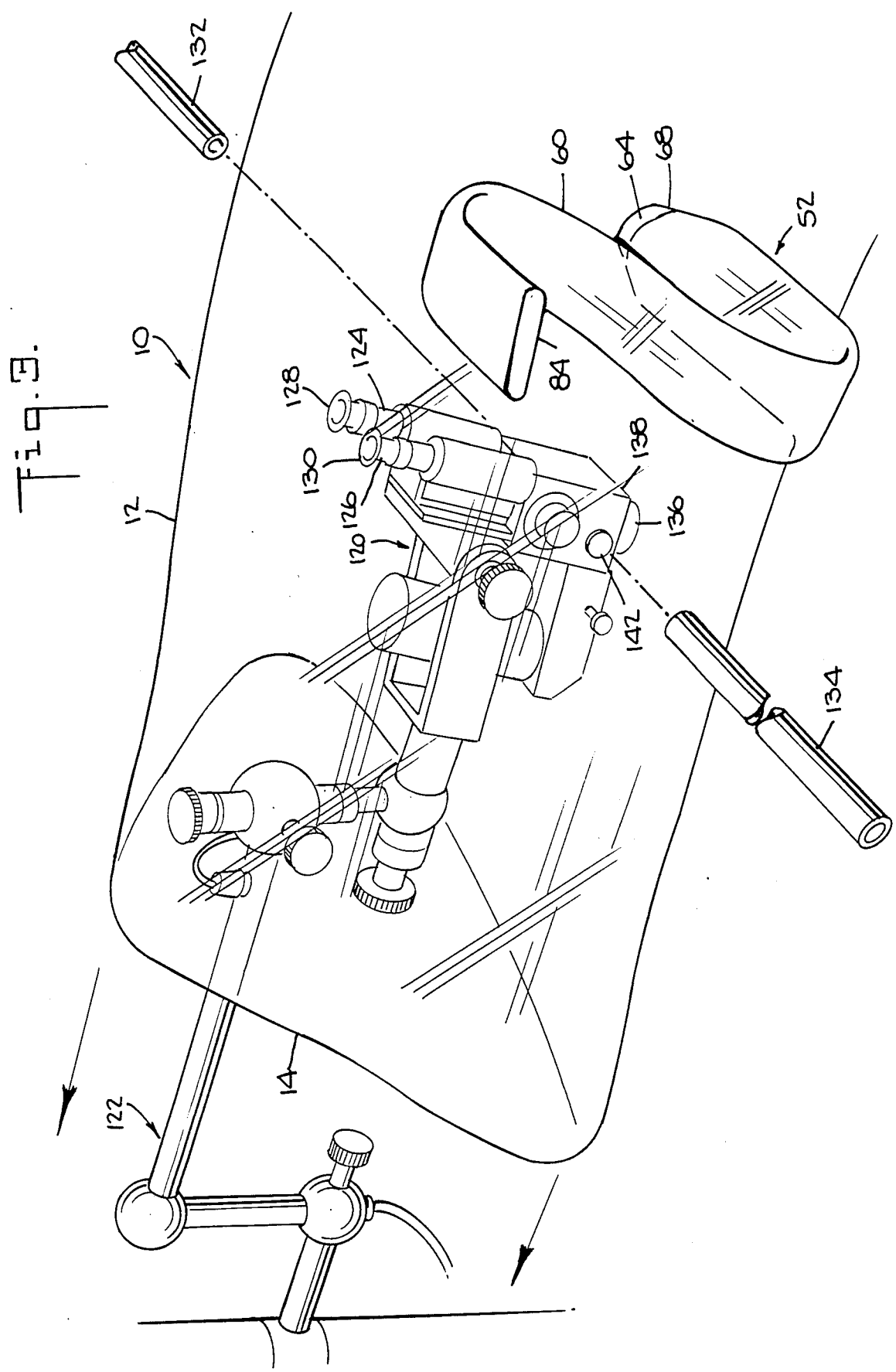

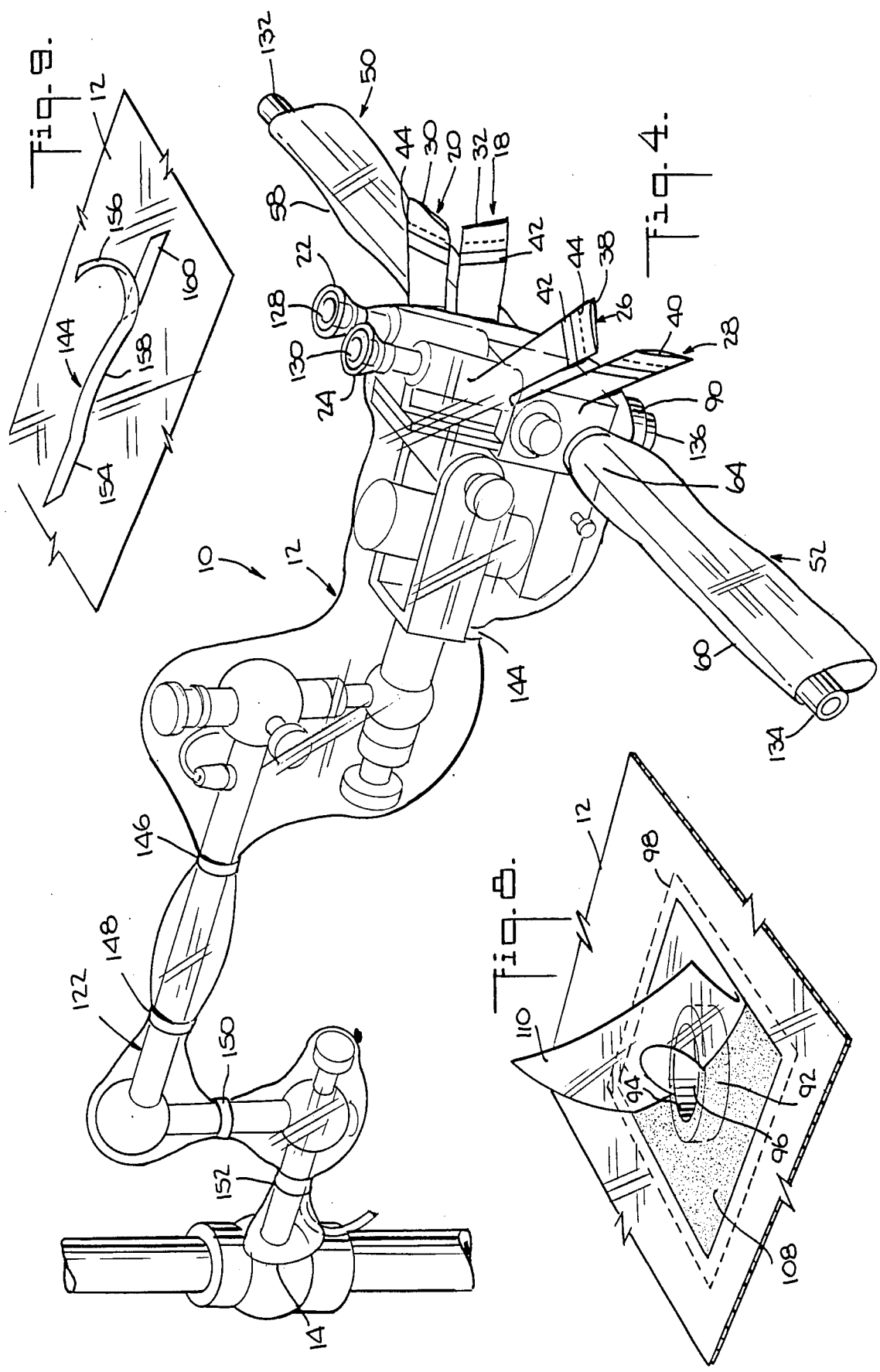

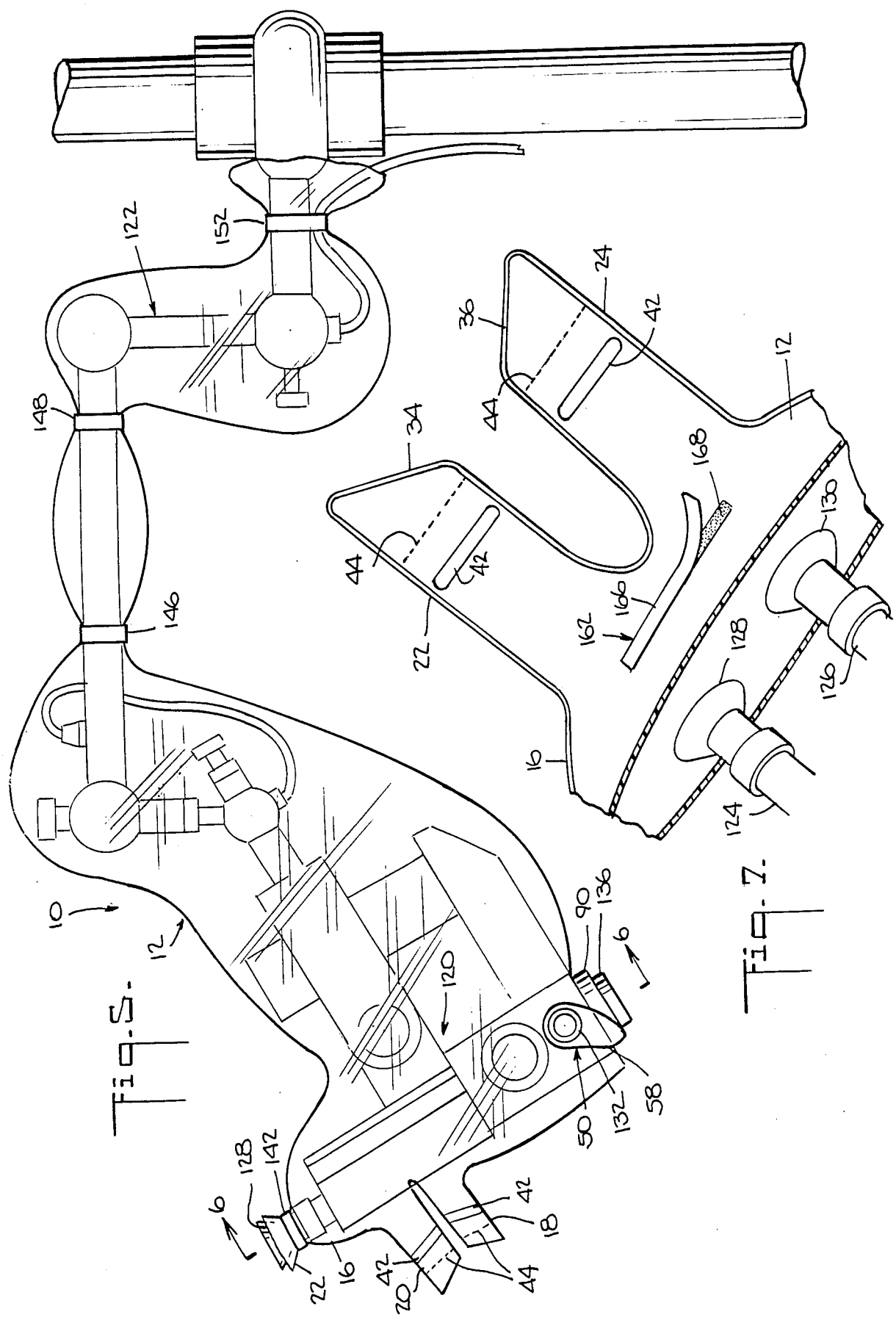

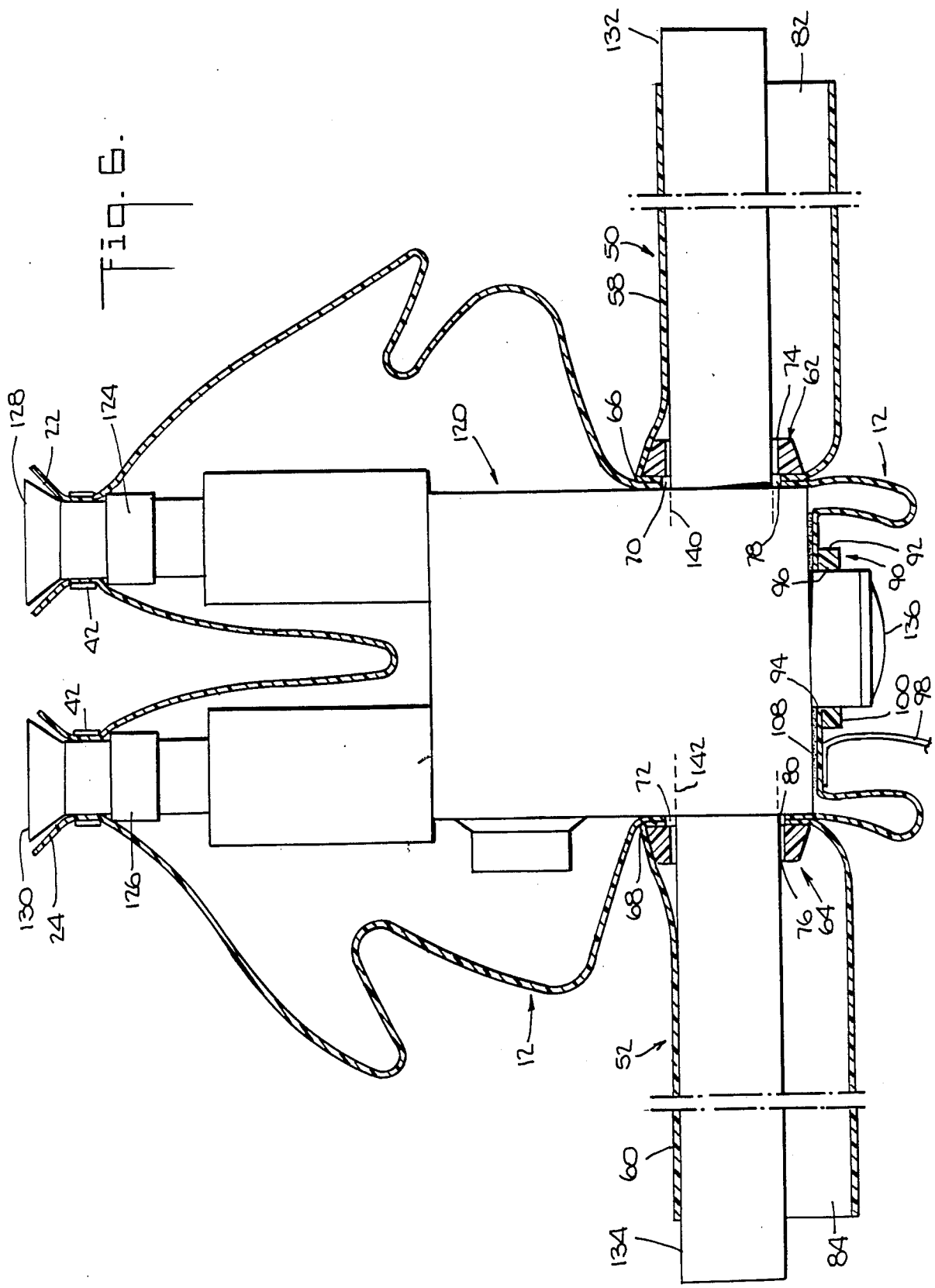

MICROSCOPE DRAPE

BACKGROUND OF THE INVENTION

This invention relates to microscope drapes that form a disposable sterile covering for surgical microscopes, and more particularly to a novel microscope drape with a one-piece main cover and one or more sleeve portions that have a reinforced joint with the main cover.

Microscopes used for surgery are generally permanent fixtures in an operating room, and often have an articulated cantilever support arrangement to facilitate movement of the microscope over an operating zone. Such microscopes can include, in addition to ocular portions, one or more viewing tubes or laser arms that project away from the microscope housing. Since an operating room usually requires sterile conditions for all furnishings, it is common practice to cover the microscope and any associated support structure with a disposable sterile covering or drape.

The microscope drape generally remains on the microscope during the performance of a surgical operation and ideally does not interfere with any of the functions of the microscope. Microscope drapes are normally replaced just prior to an operation to ensure that the microscope covering is substantially sterile during an operation.

In order to effectively cover the microscope, along with any projecting viewing tubes or laser articulating arms and associated microscope support structure, it is usually necessary to form the microscope drape with one or more sleeve-like portions to accommodate the projecting viewing tubes. Because it is not feasible to custom fit a drape to a microscope, the drape is normally made oversize and secured at predetermined locations on the microscope structure to take up undesirable slack. Since the microscope and its support structure have an irregular periphery, the securement of the drape around the microscope structure usually causes stretching or tension at some portions of the drape, especially at the joint between the main cover portion and the sleeve-like extensions.

U.S. Pat. Nos. 3,528,720; 3,698,791, and 4,266,663 show microscope drapes with sleeve-like extensions that are formed to extend from a main cover portion of the drape. The sleeve-like extensions as well as the main cover are a continuous integral structure. However, the main cover portion is made in at least two pieces that are seamed or heat welded at their edges. During installation of the drape upon a microscope, the sleeve-like extension and the main cover portion are secured to corresponding microscope structures. If the points of securement of the drape are in close proximity to the joint between the sleeve-like extension and the main cover portion, there is likelihood of a tension buildup at the joint or seams that can cause the drape material to stretch, rip or rupture.

A further problem with microscope drapes of the type described is that the material used to form the drape usually must have a minimum lateral width equivalent to the width of the main cover portion and the lateral extension of each sleeve from the main cover portion. Since the lateral width of the main cover portion is often substantially less than the overall lateral distance between the ends of the sleeve-like extensions, a substantial amount of material must be sheared or otherwise removed from the stock material used to form the drape. If the removed material cannot be used there is considerable waste.

It is thus desirable to provide a microscope drape with a one-piece seamless main cover portion and sleeve-like extensions that have a reinforced joint between the sleeve and the main cover portion.

OBJECTS AND SUMMARY OF THE INVENTION

Among the several objects of the invention may be noted the provision of a novel microscope drape, a novel microscope drape that includes one or more sleeve-like extensions for accommodating respective laser articulating arms or viewing tubes of a microscope, a novel microscope drape having sleeve-like extensions and a substantially seamless one-piece main cover portion, a novel microscope drape having a reinforced joint between a sleeve-like extension and a main cover portion, a novel microscope drape having a predetermined stress distribution path for distributing stress at a joint between a sleeve-like extension and a main cover portion, a novel microscope drape having extension sleeves that can be provided at any preselected location on a main cover portion, and a novel method of covering an operating microscope.

Other objects and features of the invention will be in part apparent and in part pointed out hereinafter.

In accordance with the present invention, the microscope drape includes a one-piece substantially tubular main body, elongated in a longitudinal direction and having an open end and an opposite closed end. The opposite closed end is provided with a plurality of cylindrical extensions for enclosing the ocular portions of a microscope. The main body portion is a one-piece enveloping structure that does not require seaming or heat welding to form the substantially tubular configuration and thus has no longitudinal edge seams.

In one embodiment of the invention, the drape is provided with a pair of sleeve-like extensions on the main body portion. Each of the sleeve-like extensions include a flexible sleeve member having one end portion joined to the main body portion with an annular reinforcement member. The sleeve member, the reinforcement member and the main body portion are preferably heat welded to each other.

The opening in the annular reinforcement member aligns with an opening in the main body portion to permit communication between the sleeve member and the interior of the main body portion.

The main body portion is also provided with an objective lens cover and housing assembly. The lens cover housing assembly includes a soft deformable locating ring that collars and releasably grips the periphery of the objective lens of the microscope. A detachable lens cover sheet which covers the locating ring of the microscope drape is removed when the drape installation is completed.

The microscope drape also includes removable adhesive strips on the main body portion for securing the microscope drape around the microscope and its associated support structure. Adhesive stripes are provided on the main body portion and the sleeve members for further securement of the drape and to take up any undesirable slack in the drape.

Another embodiment of the microscope drape includes a main body portion similar to that of the first embodiment but provided with a single sleeve-like extension secured to the main body portion in the same manner as the sleeve-like extensions of the previously described embodiment. The single sleeve-like extension thus includes an annular reinforcement member to provide a reinforced joint between the sleeve member and the main body portion.

Each embodiment of the microscope drape can be folded and enclosed in a single package to ensure sterility of the drape until the drape is ready for use.

In using he microscope drape of either embodiment, the drape is unfolded and extended to its full width and length. The open end of the drape is drawn over the microscope and its associated support structure. The drape is oriented in a predetermined position on a microscope by engaging the objective lens cover and housing assembly onto the objective lens of the microscope.

Extension tubes or laser articulating arms of the microscope are assembled to the microscope through the sleeve-like extensions of the drape. Undesirable slack portions in the drape are taken up by tying with adhesive strips provided on the drape. The drape can also be folded upon itself in the areas where adhesive stripes are provided to take up further slack.

In this manner the drape substantially encloses the entire surface portion of the microscope and its support structure, thus providing a sterile covering for the microscope.

The invention accordingly comprises the constructions and method hereinafter described, the scope of the invention being indicated in the claims.

DESCRIPTION OF THE DRAWINGS

In the accompanying drawings,

FIG. 1 is a simplified plan view of a microscope drape incorporating one embodiment of the invention;

FIG. 2 is an enlarged fragmentary perspective view thereof with a partially unfolded sleeve;

FIG. 3 is a fragmentary perspective view thereof prior to installation on an operating microscope;

FIG. 4 is a perspective view thereof after installation on an operating microscope;

FIG. 5 is a side elevation view thereof after installation on an operating microscope;

FIG. 6 is a sectional view taken on the line 6—6 of FIG. 5;

FIG. 7 is an enlarged fragmentary perspective view thereof prior to installation on an ocular portion of the microscope;

FIG. 8 is an enlarged fragmentary perspective view of a lens cover and housing assembly thereof;

FIG. 9 is an enlarged fragmentary perspective view of a securement portion thereof;

Corresponding reference characters indicate corresponding parts throughout the several views of the drawings.

DETAILED DESCRIPTION OF THE INVENTION

Figure 10:
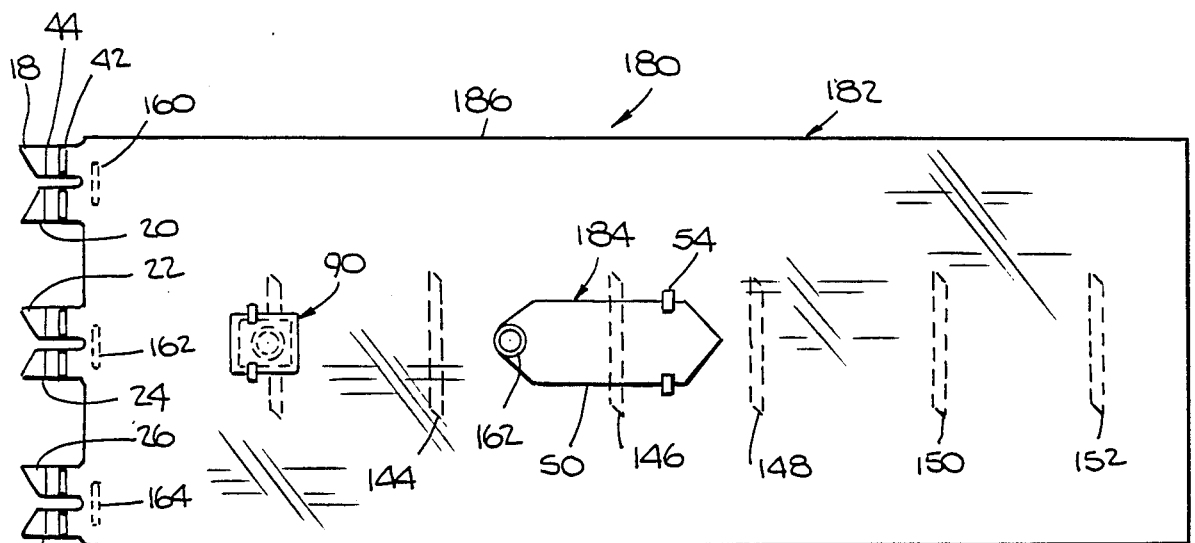
FIG. 10 is a simplified plan view of another embodiment thereof.

A microscope drape incorporating one embodiment of the invention is generally indicated by the reference number 10 in FIG. 1.

The microscope drape 10 includes a main cover or main body portion 12 that is elongated in a longitudinal direction. The main body portion 12 is preferably a one-piece substantially tubular structure that is substantially seamless, and can be formed of a relatively thin transparent sterilizable plastic material approximately 2 mm. thick. Polyethylene, polypropylene or other suitable polymer or copolymer film having the properties of flexibility and softness have been found adequate.

As used herein, the term seamless in reference to the substantially tubular structure of the main body portion 12 is intended to refer to a characteristic of the main body portion 12 in its direction of elongation, and does not include the end portions thereof.

The main body portion 12 has an open end portion 14, and a closed end portion 16 formed with three pairs of substantially cylindrical extensions 18,20; 22,24 and 26,28. Each pair of the cylindrical extensions 18,20; 22,24; and 26,28 have respective oppositely inclined free end portions 30,32; 34,36; and 38,40. A relatively thin strip of malleable metal 42 such as aluminum, is attached to each of the cylindrical extensions 18-28 by any suitable known means. The strip thus has the ability to be bent using a very slight bending force and hold the bent shape in the manner described in U.S. Pat. No. 4,561,540.

A line of weakness 44 is formed on the cylindrical extensions 18-28 intermediate the inclined free end portions 30-40 and the metallic strip 42.

The main body portion 12, in a collapsed condition such as shown in FIGS. 1 and 2, includes two folded longitudinal side edges 46 and 48. A pair of laterally aligned sleeve-like extension means 50 and 52 (shown folded in FIG. 1) are provided on the main body portion 12 laterally spaced from the folded side edges 46 and 48.

It should be noted that the folded side edges 46 and 48 do not indicate a seam or heat weld line but represent the width of the main body portion in its collapsed condition.

The sleeve-like extension means 50 and 52 respectively include generally tubular sleeve members 58 and 60, formed of the same material as the main body portion 12. As most clearly shown in FIG. 6, the sleeve members 58 and 60 include respective end portions 66 and 68 joined to annular reinforcement members 62 and 64, and opposite open end portions 82 and 84. Removable tacking strips 54 hold the sleeve members 58,60 in a folded condition until the drape 10 is ready for use.

Preferably, the reinforcement members 62 and 64 are formed of a suitable soft, flexible and deformable thermoplastic rubber material such as sold under the trademark Kraton ® manufactured by Shell Chemical Company. The sleeve end portions 66 and 68 are bonded or heat welded, for example, to respective undersides 70 and 72 of the reinforcement members 62 and 64.

The reinforcement members 62,64 and the sleeve end portions 66,68 are also bonded or heat welded to the main body portion 12 such that respective reinforcement member openings 74 and 76 (FIG. 6) align with respective main body portion openings 78 and 80. Under this arrangement, the joint between the sleeve-like extension means 50,52 and the main body portion 12 is defined by the common bond between the reinforcement members 62,64, the main body portion 12 and the sleeve end portions 66 and 68 as well as the reinforcement members 62 and 64.

Thus the main body portion 12 is heat welded to the reinforcement members 62 and 64 at the periphery of the openings 74 and 76 in the main body which align with the reinforcement members 62 and 64. The heat welding of the main body portion 12 and the sleeve end portions 66 and 68 to the reinforcement members 62 and 64 is accomplished in any suitable known manner. If desired, adhesive bonding can be used instead of heat welding.

It should be noted that the diameter of the sleeve members 58 and 60 can exceed the outside diameter of the annular reinforcement members 62 and 64. Thus the end portions 66 and 68 of the sleeve members 58 and 60 can be tapered slightly to the reinforcement members 62 and 64 as shown in FIG. 1.

The microscope drape 10 further includes an objective lens cover and housing means 90 (FIG. 1) on the main body portion 12 proximal the closed end portion 16 and laterally intermediate the sleeve-like extension means 50 and 52. The lens cover and housing means 90 includes an annular member 92 (FIGS. 2, 3 and 6) formed of a soft, deformable foam material such as medium density closed cell polyethylene. The annular member 92 is bonded to the outside surface of the main body portion 12 in any suitable known manner, in alignment with an objective lens opening 94 in the main body portion 12. The annular member 92 is of predetermined height to project a predetermined amount from the outside surface of the main body portion 12.

A generally rectangular lens cover member 98, preferably formed of an opaque plastic film such as Mylar film, backed with an acrylic adhesive for example, is detachably secured to a free end portion 100 of the annular member 92 to cover the opening 96 in the annular member 92. To facilitate detachment of the lens cover member 98 from the annular member 92, a thin plastic release film (not shown) is bonded to the free end portion 100 of the annular member 92, and the lens cover member 98 is detachably secured to the release film. The lens cover member 98 is also tacked to the main body portion 12 by releasable adhesive strips 104 and 106 (FIGS. 1 and 2). The lens cover member 98 thus covers the opening 94 of the main body portion 12 and the opening 96 of the annular member 92.

A layer of adhesive material 108 is provided on the inside surface of the main body portion 12 along an area surrounding the opening 94. The adhesive layer 108 is covered by a generally rectangular removable protective cover sheet 110.

The microscope drape 10 is used to cover a microscope 120 (FIG. 3) and its associated support structure, generally indicated by the reference number 122. Both the microscope 120 and the support structure 122 are shown in simplified schematic form. The microscope 120 includes a pair of oculars 124 and 126 with respective eyepieces 128 and 130. A pair of detachable laser articulating arms 132 and 134 of a surgical laser aiming device (not shown) extend from opposite reception portions 140 and 142 of the microscope 120. An objective lens 136 is provided at a base portion 138 of the microscope 120.

The microscope drape 10, prior to use, is preferably folded to a convenient size and stored in a sealed package (not shown) that ensures the sterility of the microscope drape 10 until it is ready for use.

In using the microscope drape 10, the drape is unfolded on a sterile table (not shown) to its full width and extent as shown in FIG. 1.

Prior to placement of the microscope drape 10 on the microscope 120, the laser articulating arms 132 and 134 are temporarily removed from the reception portions 140 and 142 of the microscope 120. The unfolded drape 10 is expanded at the open end 14, as shown in FIG. 3, to permit placement of the main body portion 12 onto the microscope 120 and the associated microscope support structure 122.

The drape 10 is positioned such that the objective lens opening 94 and the annular member 92 of the lens cover and housing means 90 align with the objective lens 136 of the microscope 120. The removable protective sheet 110 on the adhesive layer 108 is removed from the inside surface of the main body portion 12 to expose the adhesive layer 108 around the objective lens opening 94. The annular member 92 is placed around the objective lens 136 of the microscope 120 such that the adhesive layer 108 is pressed against the base portion 138 of the microscope 120 to secure the position of the annular member 92 as shown in FIG. 6.

After the annular member 92 has been suitably fixed in position on the microscope 120, other portions of the microscope drape 10 are appropriately positioned. For example, the cylindrical extensions 22 and 24 are fitted over the oculars 124 and 126, and the sleeve member 58 and 60 are substantially aligned with the laser arm receiving portions 140 and 142. The sleeve members 58 and 60 are unfolded and extended, and the respective laser articulating arms 132 and 134 are passed through the open ends 80 and 82 of the sleeve members 58 and 60 for reattachment to the receiving portions 140 and 142 of the microscope.

Adhesive strips such as 144, 146, 148, 150 and 152 are provided on the main body portion 12. Each adhesive strip 144-152, as shown in FIG. 9, includes opposite adhesive end portions 154 and 156 and a nonadhesive midportion 158. The adhesive end portions 154 and 156 adhere to adhesive release sections such as 160 bonded to the main body portion 12. Thus the adhesive strip 144, for example, is easily removed from the microscope drape 10 without causing damage to the main body portion 12. The adhesive strips 144-152 are used to secure the main body portion around the microscope structure in the manner shown in FIG. 4.

Additional adhesive securing means such as 160, 162 and 164 (FIG. 1) are provided near the closed end portion 16 adjacent the cylindrical extension pairs 18,20; 22,24; and 26,28. Referring to FIG. 7, the adhesive securing means 162 which is identical to the adhesive securing means 160 and 164, includes a protective removable nonadhesive strip 166 that covers a double sided adhesive stripe 168 bonded to the main body portion 12.

After the cylindrical extensions 22 and 24 have been fitted over the oculars 124 and 126, the nonadhesive strip 166 is removed to expose the adhesive stripe 168. Any undesirable slack in the area of the cylindrical extensions 22 and 24 can be taken up by folding the adhesive stripe 168 against itself.

The metallic strips 42 on the cylindrical extensions 22 and 24 are bent around the oculars 124 and 126 in the manner shown in FIG. 6. The metallic strips 42 thus form a collar around the oculars 124 and 126 to securely position the cylindrical extensions 22 and 24 in a predetermined position. The inclined end portions 34 and 36 of the cylindrical extensions 32 and 24 are removed by tearing at the respective lines of weaknesses 44 to permit access to the eyepieces 128 and 130.

The cylindrical extensions 18,20 and 26,28 of the drape 10 which do not accommodate an ocular portion of the microscope 20 are available for microscopes of different construction than the microscope 120. The microscope drape 10 thus has the versatility of accommodating a variety of different microscope structures.

A plurality of adhesive securing means 170, similar to the adhesive securing means 160, are provided on the arm members 58 and 60 to take up any undesirable slack in the sleeve members 58 and 60 when positioned over the laser articulating arms 132,134.

After the microscope drape 10 has been appropriately positioned to envelop the microscope 120 and the support structure 122, the lens cover member 98 of the lens housing and cover means 90 is removed from the free end portion 100 of the annular ring member 92 to expose the objective lens 136 of the microscope 120.

When the microscope drape 10 is being securely positioned on the microscope 120, tension buildup can occur in the drape material, especially at the area of the joint between the sleeve members 58 and 60, and the main body portion 12. The reinforcement members 62 and 64 provide a substantially uniform stress path for any tension forces present in the sleeve members 58,60 and the main body portion 12 in the area of the reinforcement members 62 and 64. The microscope drape 10 is thus capable of safely withstanding a predetermined level of stress at the sleeve joint and directing the stress along a predetermined stress path thereby minimizing the buildup of damaging stress concentrations.

Another embodiment of the microscope drape is generally indicated by the reference number 180 in FIG. 10.

The microscope drape 180 includes a main body portion 182 substantially similar to the main body portion 12. However the main body portion 182 is provided with a single sleeve-like extension means 184 located midway between the opposite folded longitudinal edges 186 and 188 of the microscope drape 180 in its collapsed condition.

The sleeve-like extension means 184 is identical to the sleeve-like extension means 50 and 52. In addition, the microscope drape 180 is otherwise identical to the microscope drape 10.

Figure 11:
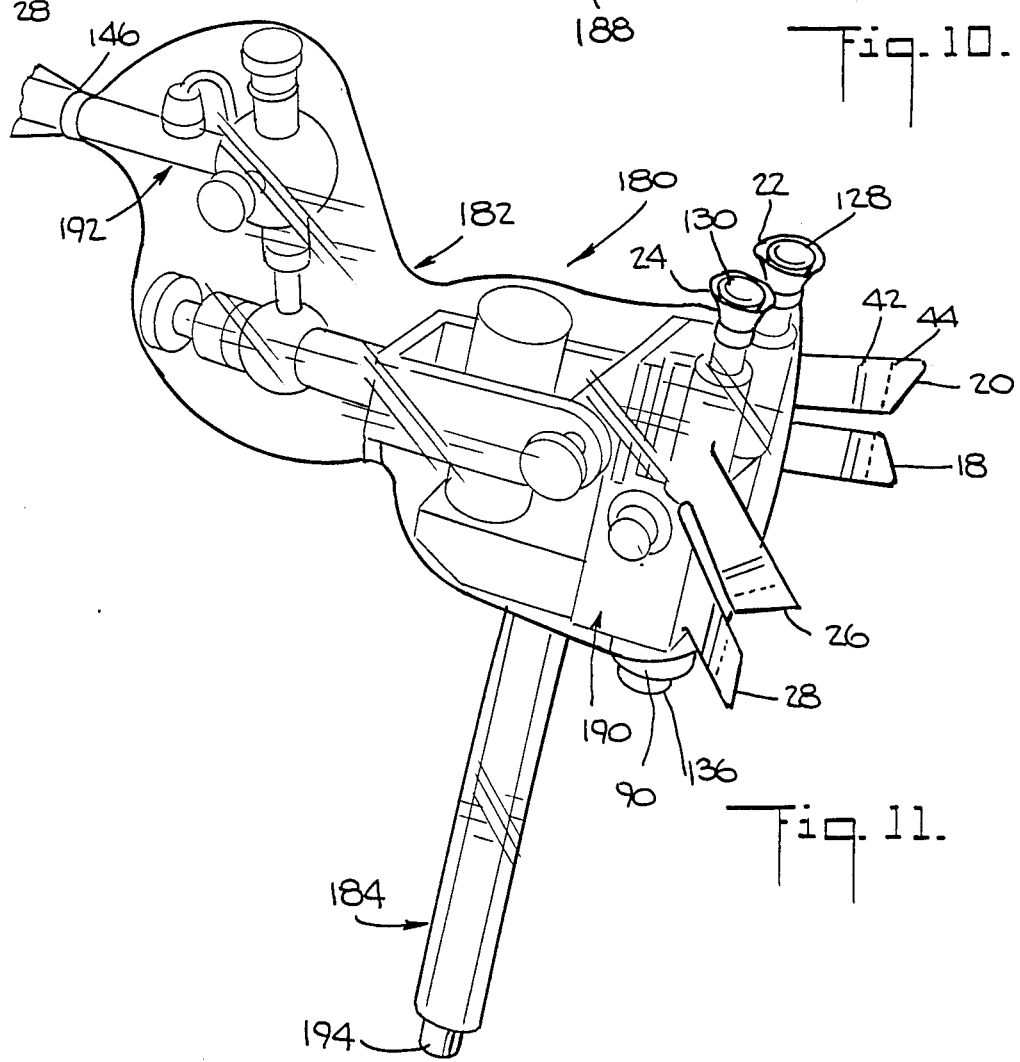
FIG. 11 is a simplified perspective view thereof after installation on an operating microscope.

The microscope drape 180, when expanded in a manner similar to that previously described for the microscope drape 10, covers a microscope 190 and its associated microscope support structure 192 as shown in FIG. 11. The microscope 190 includes a single laser articulating arm 194 accommodated in the sleeve-like extension means 184 of the microscope drape 180.

Some advantages of the present invention evident from the foregoing description include a microscope drape having a one-piece, seamless, substantially tubular main body portion and sleeve-like extensions. A further advantage of the present invention is that the absence of seams along the main body portion provides a stronger structure than a microscope drape which includes seams, since the seams are usually an area of weakness.

The microscope drape can also be provided with any selected number of sleeve-like extensions at any selected location on the one-piece, seamless, substantially tubular main body portion.

The reinforcement member which is provided at the joint between the sleeve-like extension and the main body portion provides a uniform stress path for any tensions exerted on the sleeve member during covering of the microscope with the microscope drape. The reinforcement member, by minimizing stress concentrations at the sleeve joint, helps assure against rips, tears or other possible tension damage at the joint between the sleeve member and the main body portion.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A disposable microscope drape for covering an operating microscope having ocular and objective portions, and a support portion, said drape comprising,
   (a) an elongated main body portion elongated in a longitudinal direction, for covering said support portion, said ocular portion and said objective portion of said microscope, said main body portion being formed of flexible sheet material and having opposite end portions, one of said end portions being open, the other said end portion being substantially closed for positioning at the ocular and objective portions of said microscope,
   (b) at least one flexible sleeve member having a first sleeve end portion joined to said main body portion, said sleeve member having an opposite free end portion, and
   (c) reinforcing means provided at the junction between said first sleeve end portion and said main body portion to strengthen the joint between said first sleeve end portion and said main body portion.

2. The drape as claimed in claim 1 wherein said main body portion is expandable to a substantially tubular shape, said main body portion being substantially seamless intermediate said open and closed end portions.

3. The drape as claimed in claim 1 wherein said main body portion is a one-piece formation.

4. The drape as claimed in claim 1 wherein said main body portion is collapsible to a substantially flat condition with oppositely disposed elongated folded side edges, said sleeve member being joined to said main body portion intermediate said folded side edges.

5. The drape as claimed in claim 4 wherein two of said sleeve members are joined to said main body portion intermediate said folded side edges.

6. The drape as claimed in claim 5 wherein said sleeve members are joined to said main body portion with a predetermined lateral spacing less than the distance between said folded side edges.

7. The drape as claimed in claim 1 wherein said sleeve member is a substantially seamless one-piece formation.

8. The drape as claimed in claim 1 wherein said reinforcement means comprise a reinforcement member joined to said sleeve member at said first sleeve end portion to define a predetermined stress path to permit said drape to withstand a predetermined level of stress at the joint between said main body portion and said sleeve member and direct the stress at said joint along said predetermined stress path.

9. The drape as claimed in claim 8 wherein said reinforcement member is an annular member.

10. The drape as claimed in claim 8 wherein said reinforcement member has a central axis and a predetermined axial thickness.

11. The drape as claimed in claim 1 wherein said reinforcing means comprise an annular reinforcement member and said sleeve member is formed as a separate structure with respect to said main body portion and commonly joined with said annular reinforcement member to said main body portion.

12. The drape as claimed in claim 11 wherein said main body portion, said sleeve member and said reinforcement member are joined together by heat welding.

13. A disposable microscope drape for covering an operating microscope comprising, an elongated, flexible, tubular main body portion formed of sheet material, said main body portion having an open end and a substantially closed end, at least one flexible substantially tubular sleeve member formed separately from said main body portion, and joining means for joining said sleeve member to said main body portion, said joining means being attached to said main body portion and said sleeve member.

14. The drape as claimed in claim 13 wherein said joining means include means for defining a predetermined stress path such that tensile stress imposed on said sleeve member passes through said joining means for distribution along said predetermined stress path.

15. The drape as claimed in claim 13 wherein said joining means is of annular shape.

16. The drape as claimed in claim 15 wherein said main body portion, said sleeve member and said annular joining means are bonded together to form said joint between said sleeve member and said main body portion.

17. The drape as claimed in claim 13 wherein two of said sleeve members are joined to said main body portion.

18. A method of covering an operating microscope comprising,
   (a) forming a seamless tubular enclosure with an opening at one end and an opposite closed end for disposition on the microscope and the microscope support structure,
   (b) forming a separate substantially tubular sleeve member,
   (c) joining one end of the sleeve member to the tubular enclosure,
   (d) reinforcing the joint between the sleeve member and the tubular enclosure with a reinforcing member that defines a predetermined stress path for distrubuting tensile stresses imposed on the sleeve member at the joint.

19. The method as claimed in claim 18 including the joining of two separately formed sleeve members to the tubular enclosure in spaced relationship.

20. The method as claimed in claim 18 wherein the step of joining includes heat welding the reinforcing members to the joint between the sleeve member and the tubular enclosure.

* * * * *